United States Patent [19]

Krzyzanowski

[11] Patent Number: 5,325,866
[45] Date of Patent: Jul. 5, 1994

[54] FLEXIBLE BIOPSY FORCEPS

[76] Inventor: Jacek Krzyzanowski, 17 Oxenden Crescent, Etobicoke, Ontario M9C 4H3, Canada

[21] Appl. No.: 50,580

[22] Filed: Apr. 20, 1993

[51] Int. Cl.⁵ .............................. A61B 17/28
[52] U.S. Cl. ............................ 128/751; 606/205
[58] Field of Search .......... 606/205, 206, 207, 51, 606/52, 113, 127; 128/751

[56] References Cited

U.S. PATENT DOCUMENTS

| | | |
|---|---|---|
| 3,895,636 | 7/1975 | Schmidt . |
| 4,178,810 | 12/1979 | Takahashi . |
| 4,632,110 | 12/1986 | Sanagi . |
| 4,655,219 | 4/1987 | Petruzzi . |
| 4,763,668 | 8/1988 | Macek et al. . |
| 4,945,920 | 8/1990 | Clossick . |
| 4,953,559 | 9/1990 | Salerno . |
| 5,100,430 | 3/1992 | Avellanet et al. . |
| 5,133,727 | 7/1992 | Bales et al. . |
| 5,152,779 | 10/1992 | Sanagi . |

*Primary Examiner*—Michael H. Thaler
*Attorney, Agent, or Firm*—Shlesinger, Arkwright & Garvey

[57] ABSTRACT

There is disclosed a flexible biopsy forceps device for extracting tissue samples from a patient. The forceps device includes a long flexible sheath having a cable extending therethrough, a jaw assembly connected at one end of the cable and a handle assembly attached at the other end of the cable. The handle assembly includes a spool slidably mounted on a shaft connected to the cable and sheath in such a way that movement of the spool handle results in movement of the cable with respect to the sheath to open and close the jaws. A spool insert is provided which has two portions which fit together locking the end portion of the cable therebetween. The spool insert slides into an axial passageway in the spool and interlocks with the spool in such a way that it is irreversibly locked therewith. The jaw assembly includes a trocar which is locked with the jaw assembly using a tongue-in-groove assembly.

9 Claims, 6 Drawing Sheets

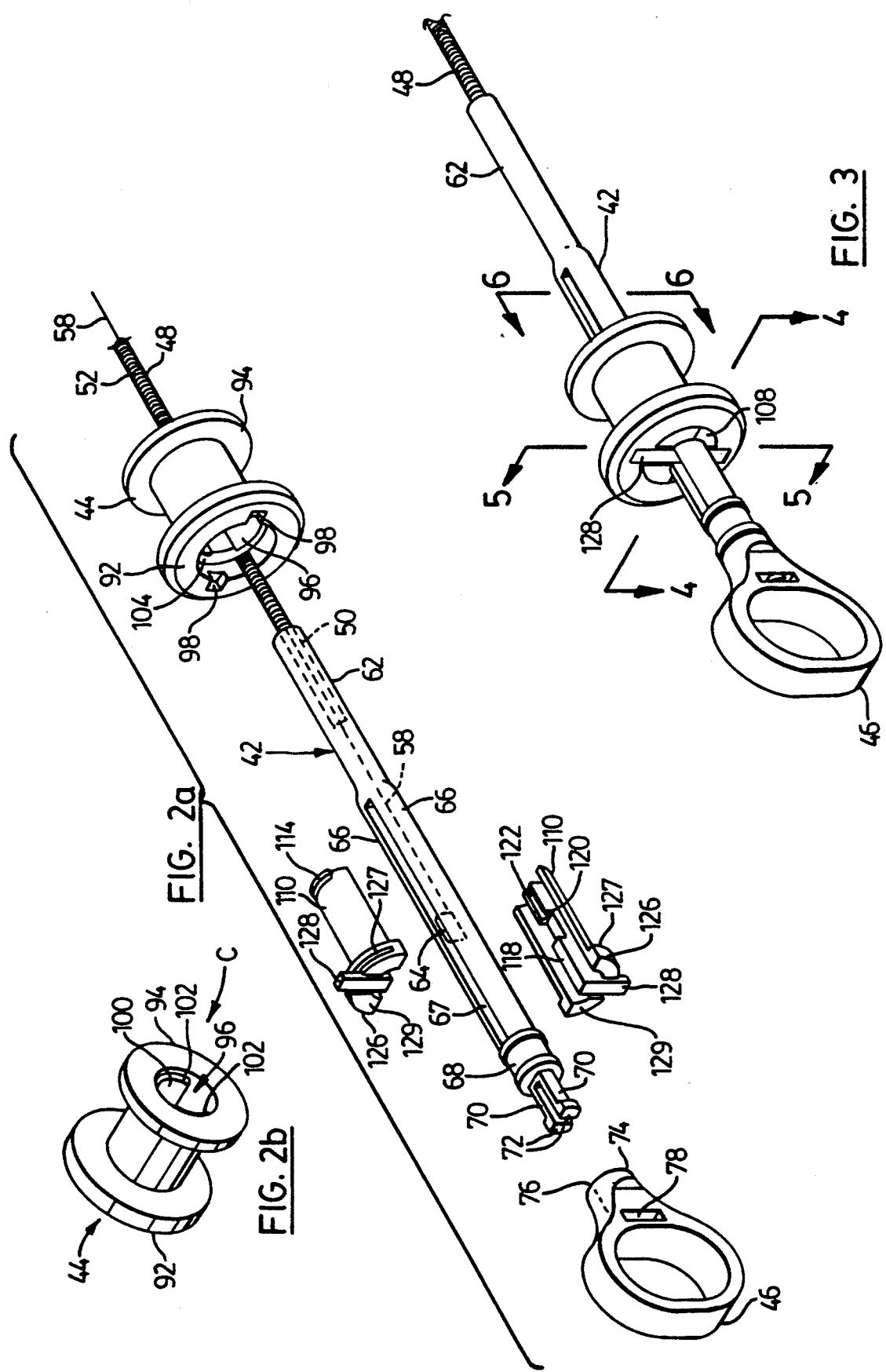

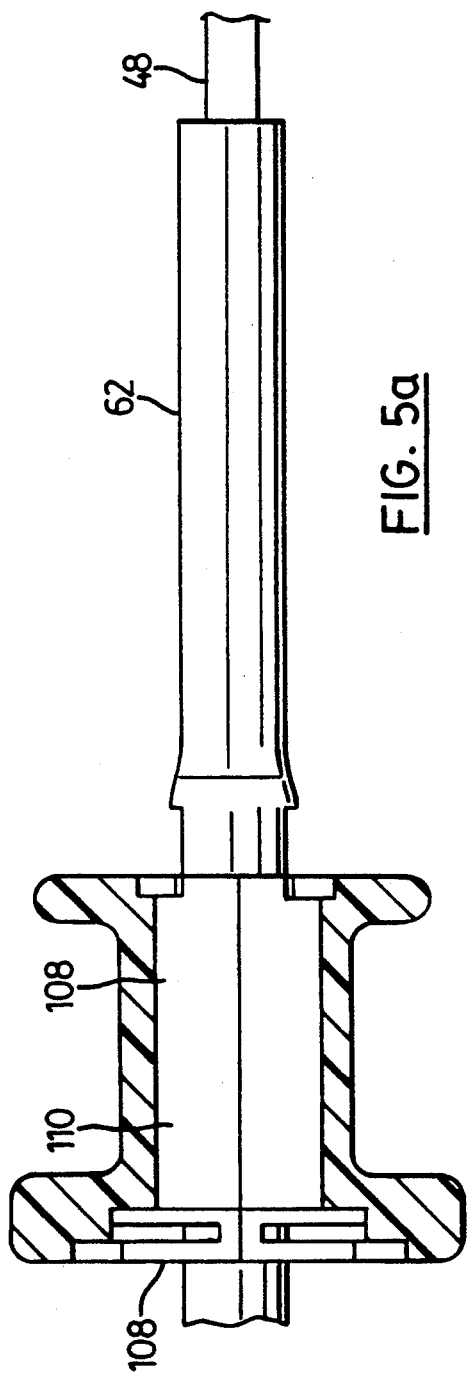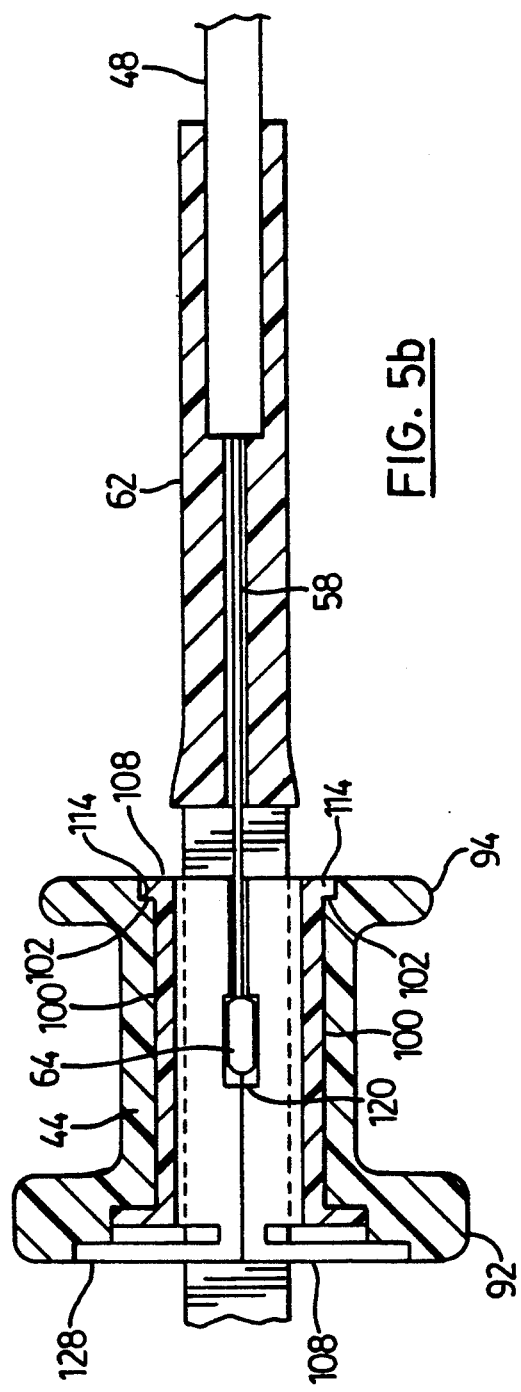

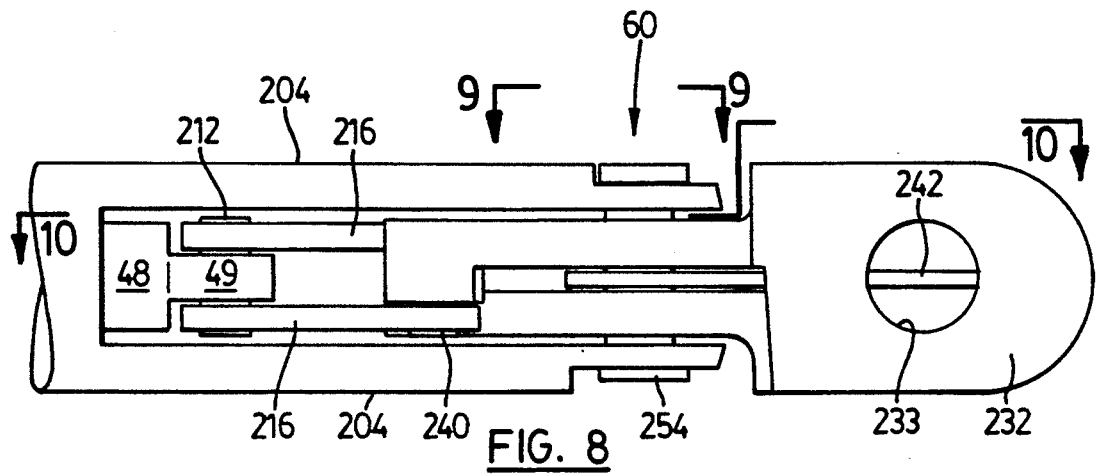
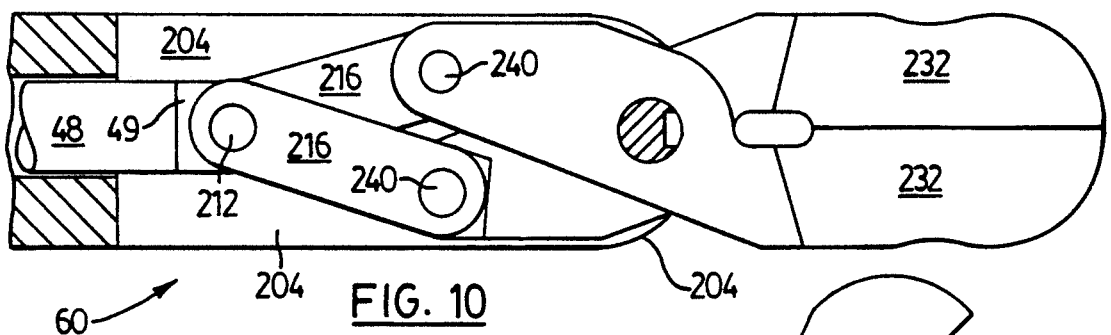
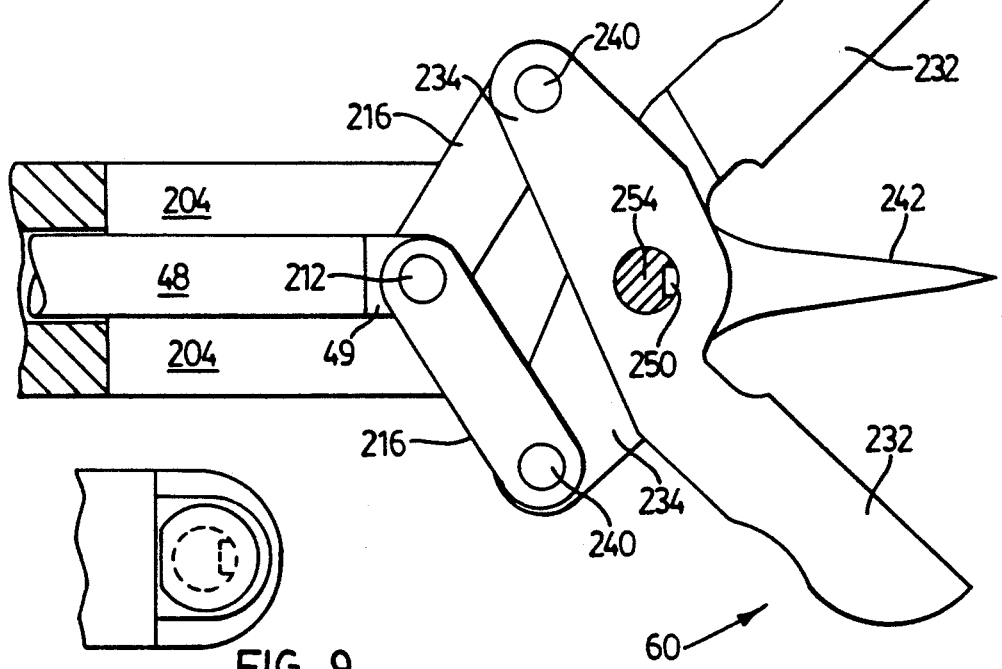

FLEXIBLE BIOPSY FORCEPS

FIELD OF THE INVENTION

The present invention relates to flexible biopsy forceps used for removing tissue samples from the interior of a patients' body.

BACKGROUND OF THE INVENTION

The ability to easily remove tissue samples (diseased or otherwise) from the interior of a patient's body, along for example the gastrointestinal tract for external ex-situ analysis is a very important part of many medical diagnostic procedures. Known devices for performing this operation include flexible biopsy forceps which are used in conjunction with an endoscope which is inserted by a doctor into the digestive tract of the patient. The biopsy forceps device comprises a long flexible sheath having a cable extending therethrough and includes a pair of pivotally connected jaws attached at one end of the cable and a handle assembly attached at the other end thereof. The handle assembly includes a spool slidably mounted on a shaft connected to the cable in such a way that movement of the spool handle results in opening and closing of the jaws. The endoscope is introduced into the patient's body and then the biopsy forceps device is inserted into the elongate channel of the endoscope and the latter is inserted into the body. The handle assembly of the forceps device is then manipulated by the operator to grip, cut and remove the desired tissue sample.

Known handle assemblies generally include a finger actuated slide or spool slidably mounted on a shaft which is rigidly connected to a thumb ring. Certain types of these handle assemblies include plugs which fit inside the spool and are secured therein by means of set screws and the like. The cable is connected to the plug and the sheath attached to the shaft so that movement of the spool and hence the plug results in movement of the cable with respect to the sheath causing the jaws to open and close. A drawback to this type of arrangement is that the set screws are prone to becoming loose and being lost which can be a great inconvenience and a potential danger during use since the jaws cannot then be properly utilized.

Another type of known handle assembly employs a spool insert which is externally threaded and the spool is internally threaded to receive the plug. The handle assemblies in these devices must be constantly checked to ensure they have not come loose. Another type of spool insert includes a pair of arms connected at a midpoint and the ends of the arms are sized and are deformable so that the insert is received in the spool in such a way so that the end portions of the arms extend beyond the ends of the spool when assembled. Such a device is disclosed in Japanese Laid-Open Utility Model Application No. 58-160010. A drawback to this type of arrangement is that the ends of the arms are prone to being broken thereby rendering the device inoperative. In addition, the arms must be strong enough to withstand stresses related to the opening and closing of the jaws while at the same time being flexible enough to deform during assembly.

Many types of flexible biopsy forceps include a trocar having a sharp point disposed between the jaws. The trocar aids in positioning and fixing the jaws with respect to the tissue to aid in removal of the tissue sample. For example, the trocar is first embedded in the tissue sample with the jaws open thereby anchoring the device so that it does not become dislodged or move around as the jaws are manipulated. In some types of trocar/jaw combinations the trocar is attached to the jaw assembly by means of a pin extending into a hole in part of the trocar and soft soldered to a housing. A drawback to this type of arrangement is that the pin can become loose during ultrasonic cleaning. Some assemblies use a trocar with an integral small tab folded outwards and inserted into a hole in the housing. A drawback to this type of arrangement is that the tab can protrude from the housing thereby presenting a sharp edge which is prone to damage the interior of the endoscope. Also, the tab can break off easily due to its small size resulting in possible loss of the trocar.

Accordingly, it is desirable to provide a flexible biopsy forceps device which provides a handle assembly wherein the finger actuated spool and associated spool insert are securely locked together and not prone to falling apart. In addition, it is desirable to provide a jaw assembly with a trocar affixed to the assembly in such a way that it is not prone to falling apart.

SUMMARY OF THE INVENTION

The present invention provides a biopsy forceps device comprising a flexible sheath and a cable extending through the flexible sheath. Included is a jaw assembly operably coupled to one end of the cable and the sheath. The forceps device includes a handle assembly operably coupled to the other end of the cable and the sheath. The handle assembly includes a shaft member and a spool slidably mountable on the shaft. The spool has first locking means which are of unitary construction with the spool. The handle assembly includes a spool insert receivable by the spool and the spool insert includes second locking means which are of unitary construction with the spool insert. The first locking means is lockingly engagable with the second locking means for irreversibly locking the spool insert and spool together. The other end of the cable is operably coupled to the spool insert when the handle assembly is assembled. Movement of the spool on the shaft moves the cable with respect to the sheath for opening and closing the jaw assembly.

According to a further aspect of the present invention, there is provided a biopsy forceps device comprising a flexible sheath and a cable extending through the flexible sheath. Included is a jaw assembly operably coupled to one end of the cable and the sheath. The forceps device includes a handle assembly operably coupled to the sheath. The handle assembly includes a shaft member and a spool slidably mountable on the shaft. The spool has a first locking means which are of unitary construction with the spool. The handle assembly includes a spool insert receivable by the spool and the spool insert includes second locking means which are unitary construction with the spool insert. The spool includes a axial passageway extending therethrough and the spool insert comprising a pair of shell members which are generally half-cylindrically shaped and receivable within the axial passageway. The first locking means comprises a pair of space slots located at a first end of the spool and a pair of spaced ridges extending into the axial passageway and having ridge end portions spaced from a second end of the spool. The second locking means comprises a outwardly protruding shoulder located at substantially a first end portion of each shell member and an outwardly protruding boss member located at a second end portion of each shell member. The boss member is resiliently deformable and sized to fit into one of the slots of the first locking means wherein boss member and the shoulder on each shell member are aligned along a line parallel to the elongate axis of the shell. One of the slots and one of the ridges are aligned along a first line parallel to the axial passageway and the other slot and ridge are aligned along a second line parallel to the axial passageway whereby the spool insert is received into the axial passageway with the shoulders located between the ridges until the shoulders pass the ridge end portion and the spool is rotated until the boss members snap into the slots. In this way, the first locking means is locking engageable with the second locking means to irreversibly lock the spool insert and the spool together. Another end of the cable is operably coupled to the spool insert when the handle assembly is assembled. Movement of the spool on the shaft moves the cable with respect to the sheath for opening and closing the jaw assembly.

BRIEF DESCRIPTION OF THE DRAWINGS

The flexible biopsy forceps device forming the present invention will now be described, by way of example only, reference being had to the accompanying drawings, in which:

FIG. 2a is an exploded perspective view, broken away, of the handle assembly of the flexible biopsy forceps device shown in FIG. 1;

FIG. 2b is a perspective view of a spool forming part of the handle assembly of FIG. 2a;

FIG. 3 is a perspective view of the handle assembly of FIG. 2 assembled for use;

FIG. 5a is a partial cross sectional view along the line 5—5 of FIG. 3 similar to FIG. 4a but rotated 90 degrees with respect to the line 4—4;

FIG. 5b is a partial cross sectional view along the line 5—5 of FIG. 3 similar to FIG. 4b but rotated 90 degrees with respect the line 4—4;

FIG. 8 is a plan view of the assembled jaw assembly of FIG. 7;

FIG. 9 is a view along the line 9—9 of FIG. 8;

FIG. 10 is a view along the line 10—10 of FIG. 8 with the jaws in the closed position; and FIG. 11 is a view similar to FIG. 10 but with the jaws in the open position.

DETAILED DESCRIPTION OF THE INVENTION

Figure 1:
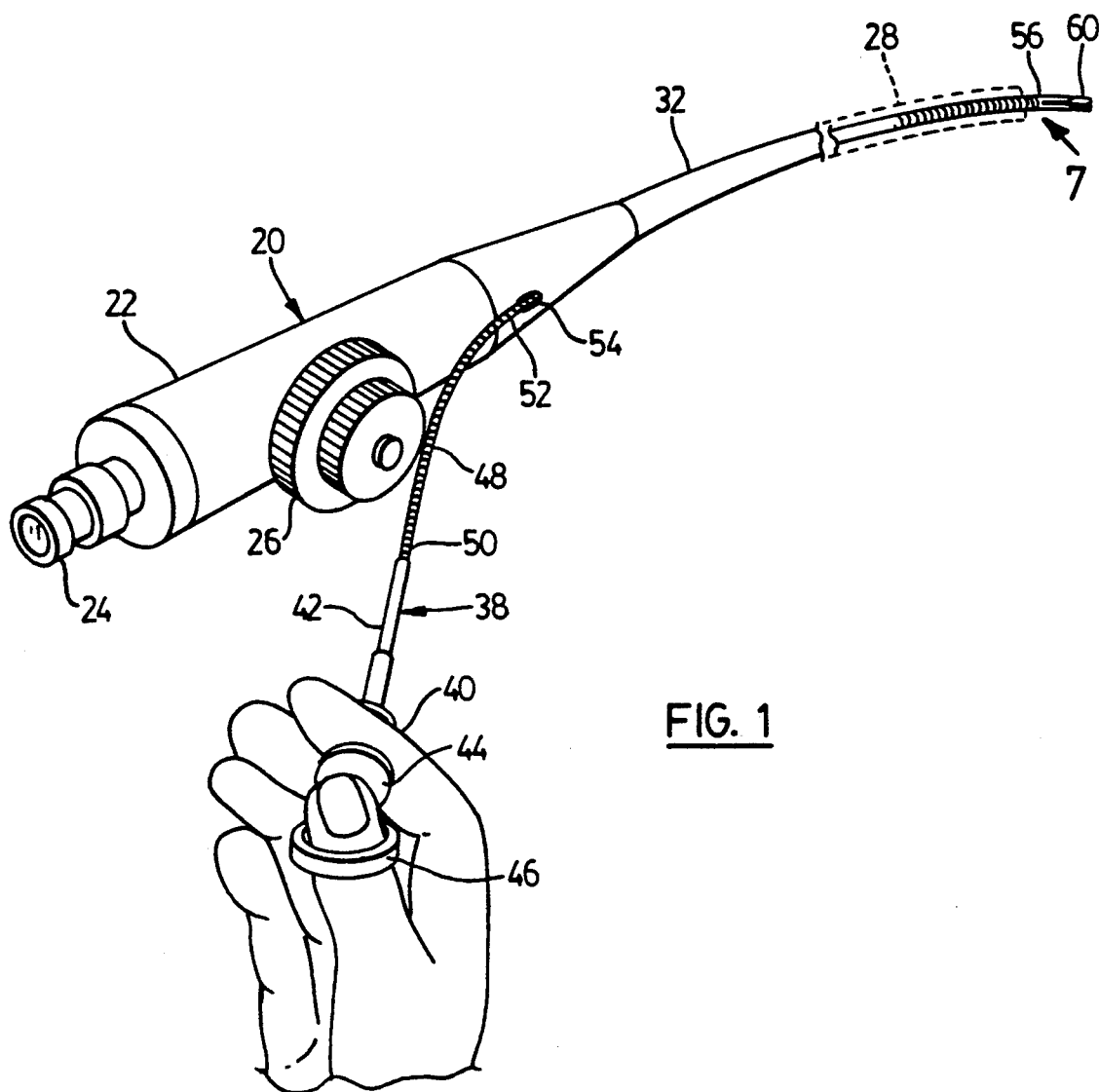
FIG. 1 is a perspective view of an endoscope provided with a flexible biopsy forceps device constructed in accordance with the present invention.
Figure 6A:
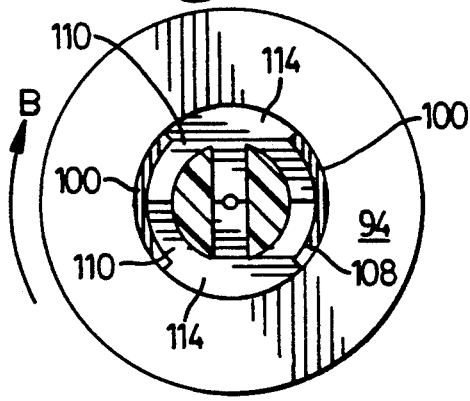
FIG. 6a is a view along the line 6—6 of FIG. 3 showing the orientation of the assembled handle assembly but prior to locking the assembly.
Figure 6B:
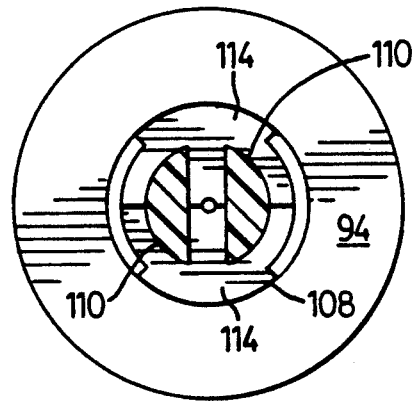
FIG. 6b is similar to FIG. 6a but showing the assembled handle assembly after rotation of the outer spool with respect to the spool insert along arrow B to lock the spool insert and outer spool together.
Figure 4A:
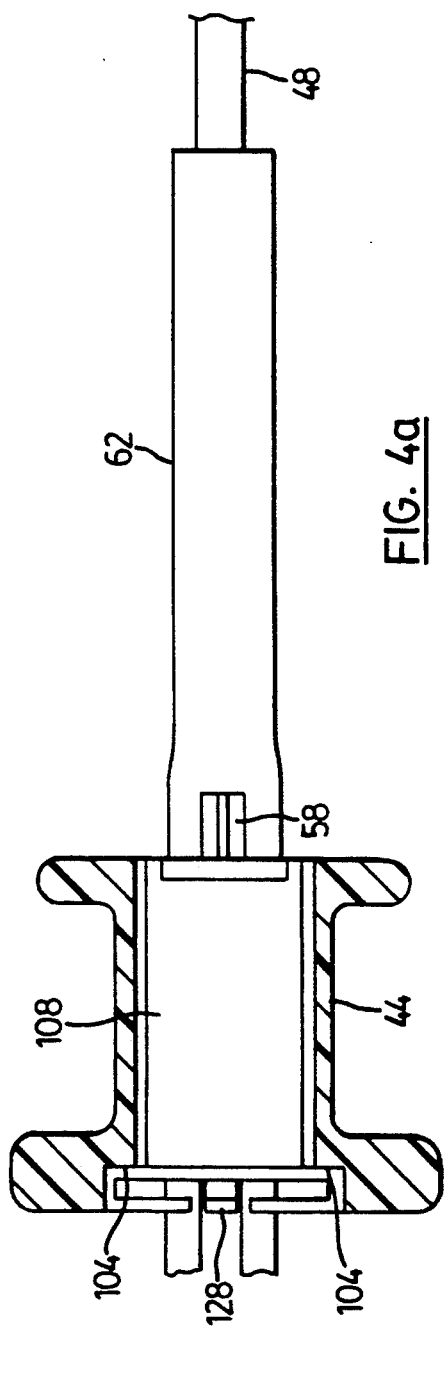
FIG. 4a is a partial cross sectional view along the line 4—4 of FIG. 3 showing the spool in cross section.
Figure 4B:
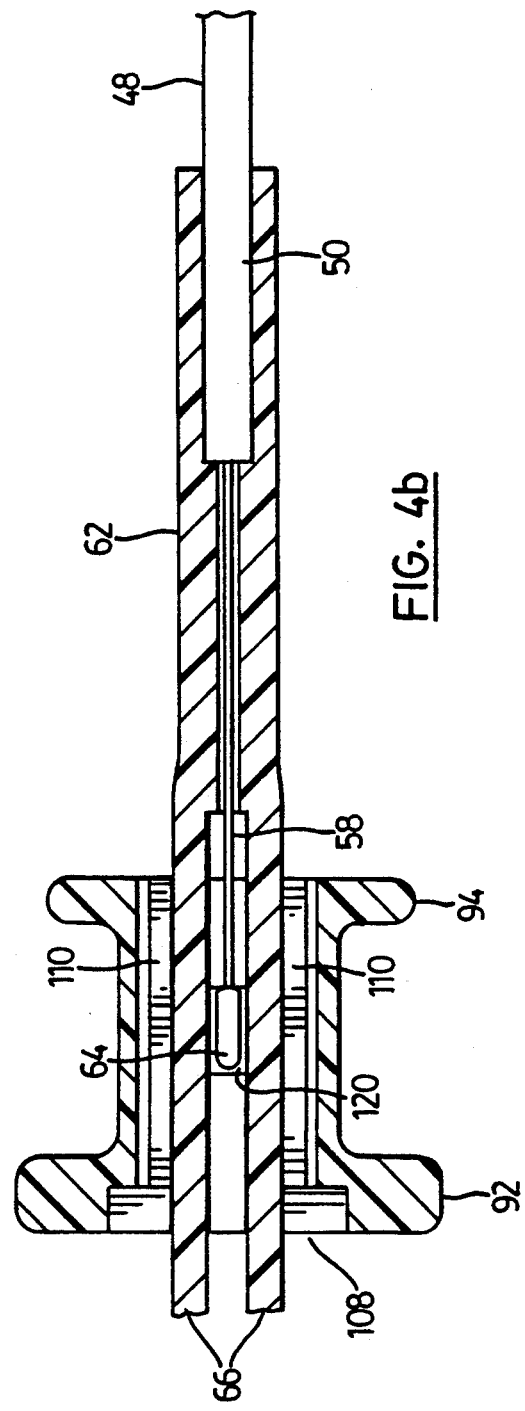
FIG. 4b is a full cross sectional view along the line 4—4 of FIG. 3.

Referring first to FIG. 1, an endoscope 20 for internal examination of patients includes a proximal head portion 22 comprising a visual observation port 24 and a deflection mechanism 26 for positioning the distal end portion 28 once the latter is in the interior of the patient. Observation port 24 is operably coupled to for example a fibre optic cable which extends through longitudinal body 32 of endoscope 20 and having a distal end portion located at the end of the endoscope. Other optical viewing systems use small CCD chips located at the distal end of the endoscope.

A flexible biopsy forceps device 38 forming the present invention includes a proximal handle assembly 40 having a shaft 42, a finger actuated spool 44 slidably mounted on the shaft and a thumb ring 46 attached to the end of the shaft. A flexible sheath 48 includes a proximal end portion 50 engaged in shaft 42, an elongate mid-portion 52 extending through an aperture 54 in the side of endoscope 20 and a distal end portion 56 protruding from distal end 28 of the endoscope when in use.

Referring to FIGS. 1 and 2, a wire cable 58 extends through sheath 48 and is operably coupled to a jaw assembly 60 located at the distal end of the sheath, the details of which will be discussed presently. Details of handle assembly 40 will now be described with particular reference to FIGS. 2a, 2b, and 5b. Shaft 42 comprises a distal hollow cylindrical portion 62 having a stepped channel diameter into which end portion 50 of sheath 48 is inserted partway (see FIG. 5b). End portion 50 is glued into cylindrical portion 62 and a stress relief member (not shown) may be included between sheath 48 and the cylindrical portion. The proximal end portion of cable 58 engaged in handle assembly 40 terminates in an enlarged cylindrical member 64, both shown in ghost outline in FIG. 2a. Shaft 42 includes a bifurcated portion comprising two spaced rods 66 attached at one end to hollow cylindrical portion 62 and at the other end to a proximal, solid cylindrical section 68. Rods 66 enclose therebetween a passageway 67. Extending from the end of cylindrical section 68 are a pair of spaced arms 70 each having outwardly projecting tongue portions 72. Thumb ring 46 includes a hollow neck portion 74 having a passageway 76 extending along the axis of the neck. Shaft 42 is attached to thumb ring 46 by squeezing together arms 70 and inserting the arms into passageway 76 until tongues 72 snap into grooves 78 located at the end of the passageway. Thumb ring 46 and spool 44 is sized and shaped to receive the thumb and index and middle fingers respectively of a user as shown in FIG. 1.

Hollow, generally cylindrically shaped spool 44 is provided with rims 92 and 94 at the ends thereof and an axial passageway 96 extending therethrough. Rim 92 is provided with two recessed slots 98 on opposite sides of passageway 96. As best seen in FIG. 2b, spool 44 includes a pair of opposed ridges 100 which extend along the interior wall of axial passageway 96 and project inwardly toward the axis of the spool. Each ridge 100 includes an end face 102 spaced from the end of passageway 96 adjacent rim 94 (best seen in FIG. 2b) and an end face 104 spaced from the end of the passageway adjacent rim 92 (see FIG. 2a). Ridges 100 are aligned with slots 98 along lines parallel to axial passageway 96. Ridges 100 and slots 98 are of one piece unitary construction with the rest of spool 44.

Referring now to FIG. 2a, handle assembly 40 includes a spool insert comprising two substantially identical, generally cylindrical half shell portions 110 fabricated by moulding for example. When assembled, the shells 110 form a spool insert referred to by numeral 108 as seen in FIGS. 3 to 6. Each cylindrical half shell portion 110 includes an outwardly projecting shoulder portion 114 located at one end of the shell on the outer surface thereof and extending part of the way around the circumference of the shell. A longitudinal web 118 is integrally formed with shell 110 on the inner surface thereof and is dimensioned to be received between arms 66 in passageway 67 of shaft 42. Web 118 includes a cut-out portion 120 sized and shaped to receive therein half of enlarged end portion 64 of wire 58 and the web further includes a trough 122 extending from cut-out portion 120 to the end of the web for receiving therein cable 58 when handle assembly 40 is assembled.

Each cylindrical half shell portion 110 includes a split rim 126 at the end of the shell spaced from shoulder portion 114 and a boss member 128 disposed between the two split rim portions with the boss member integrally formed with web 118. Split rim 126 has an inner face 127 facing shoulder 114. Web 118, boss member 128, shoulder 114 are all of one piece unitary construction with shell 110. Boss members 128 and shoulders 114 irreversibly interlock with slots 98 and ridges 100 respectively on spool 44 as will be presently discussed. Boss members 128 are flexible and may be deformed out of the plane of outer face 129 of split rim 126. Boss members 128 are aligned with shoulders 114 as best seen in FIG. 2 wherein the boss member and shoulder on each shell member are aligned along a line parallel to the elongate axis of the shell. In order to assemble handle assembly 40, cable 58 is inserted through hollow cylindrical section 62 until the end of the cable is located between arms 66 and then enlargement 64 attached to the end of the cable. Shells 110 are then aligned with webs 118 between arms 66 and are inserted into passageway 67 between the arms. Enlargement 64 is enclosed within cut-out portion 120 and the adjacent portion of wire 58 is located within trough 122.

When shells 110 have been assembled into insert 108 on shaft 42, spool 44 is oriented with insert 108 as shown in FIG. 2a with bosses 128 rotated 90 degrees with respect to slots 98. Spool 44 is then pushed over insert 108 until rim 92 abuts bosses 128 and deforms them out of the plane of end face 127 of split rim 126. At this point, shoulders 114 of shells 110 are positioned in front of ridge end faces 102 and spool 44 is then rotated 90 degrees in the direction of arrow B, see FIGS. 6a and 6b, whereby shoulders 114 come into abutting relation to ridge end faces 102, inner faces 127 come into abutting relation with ridge end faces 104 and bosses 128 snap into slots 98. Shoulders 114 abutting ridge end faces 102 and split rim faces 127 abutting ridge faces 104 prevent insert 108 moving out of passageway 96 while bosses 128 locked into slots 98 prevents rotational movement of insert 108 thereby irreversibly locking spool insert 108 within spool 44. Spool insert 108 can only be removed by breaking both bosses 128. FIGS. 4a, 4b, 5a and 5b illustrate various views of the orientation of assembled spool insert 108 within spool 44. Spool insert 108 does not protrude from the ends of spool 44 when assembled therewith.

Handle assembly 40 disclosed herein is advantageous for several reasons. Spool insert 108 comprised of the two half portions 112 are irreversibly locked within spool 44 when the handle assembly is assembled thereby circumventing the prior art problem associated with the spool insert becoming decoupled from the spool due to set screws and the like coming loose. Further, because the ends of spool insert 108 are flush with the ends of the rims on spool 44, there are no exposed spool insert parts which may be inadvertently broken off. Another advantage of the present handle assembly is that flexible bosses 128 are not under stress during the opening and closing of the jaw assembly 60 as spool 44 is moved along shaft 42. Bosses 128, in conjunction with slots 98 act to lock spool insert 108 from rotating and coming loose from spool 44 and therefore, since there is no rotational movement during opening and closing jaw assembly 60, there is no stress on bosses 128. The only stresses are experienced along the length of the spool by the thick shoulders 114 abutting end faces 102 of ridges 100 and inner surfaces 127 of split rim 126 abutting against end face 104 of the ridges.

Figure 7:
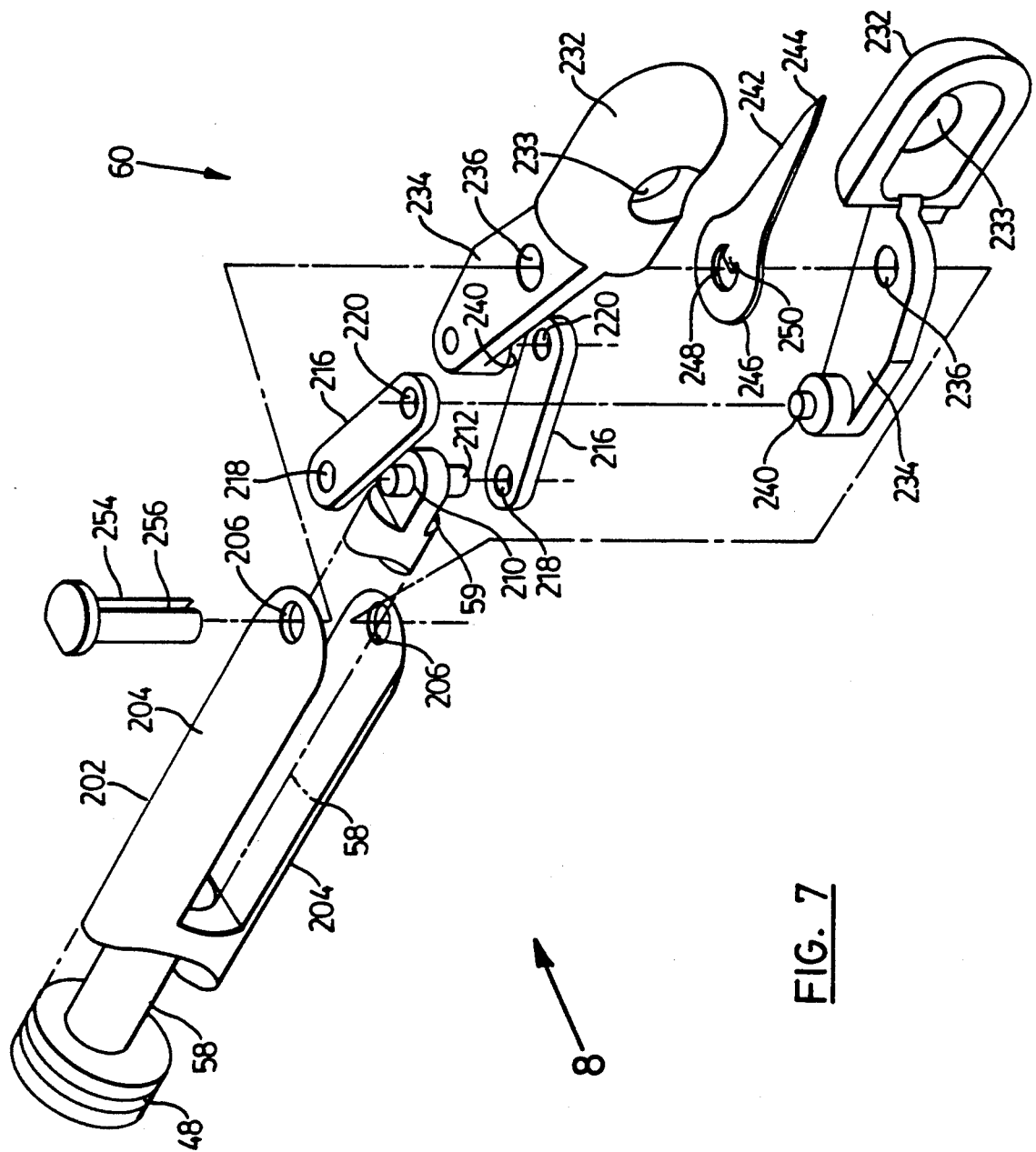
FIG. 7 is a disassembled view of the jaw assembly of FIG. 1.

Referring now to FIG. 7, an exploded view of jaw assembly 60 forming part of the present invention is illustrated. Attached to the end of sheath 48 is a bifurcated end sleeve or housing 202 through which an end portion 59 of cable 58 is inserted. End sleeve 202 comprises two spaced arms 204 each having an aperture 206 extending through the end portions thereof. The distal end portion 59 of cable 58 is provided with a hole 210 through which a rivet 212 is inserted when the jaw is assembled. A pair of link members 216 are provided and each have a hole 218 at the ends of the links through which rivet 212 is inserted thereby attaching links 212 to cable end portion 59 when jaw assembly 60 is assembled. Link members 216 are each provided with a hole 220 at the other end thereof.

Jaw assembly 60 includes a pair of jaws comprising two cups 232 each attached to a flat shank 234. Cups 232 each include a hole 233 extending therethrough so that the cups are fenestrated. Shank 234 has a hole 236 extending therethrough located between cup 232 and a pin 240 located at the end of the shank. Pins 240 are received within hole 220 of the corresponding links 216 thereby attaching cups 232 to the links.

Jaw assembly 60 includes a trocar 242 having a piercing end portion 244 and a mounting portion 246 provided with a hole 248 extending therethrough. A rectangular tab 250 integrally formed with trocar 242 extends into hole 248. When jaw assembly 60 is assembled, a rivet 254 having a groove 256 is inserted through holes 206, 236 and 248 with tab 250 received into groove 256 to form a tongue-in-groove connection thereby locking trocar 242 against rotational movement with respect to the rest of the assembly, see FIGS. 7 and 11. Rivet 254 does not rotate with respect to sleeve 202. It will be appreciated by those skilled in the art that groove 256 may be V-shaped or any other shape as long as tab 250 has a complementary shape to be received therein.

The jaws and other components of jaw assembly 60 may be economically fabricated of powdered metal to provide a strong and long lasting assembly.

In operation, with endoscope 20 positioned in the patient, the operator manipulates mechanism 26 to approach the site from which the tissue sample is to be removed. The operator then pushes biopsy forceps device 38 through aperture 54 in endoscope 20 with jaw assembly 60 closed. When the jaw assembly exits endoscope 20 as shown in FIG. 1, the jaws are opened and trocar 242 pierces the tissue sample to be taken. To open the jaws, the operator pushes spool 44 away from thumb ring 46 thereby pushing cable 58 through flexible sheath 48, best seen in FIG. 1. Referring now to FIGS. 10 and 11, as the operator pushes spool 44 away from thumb ring 46, cable end portion 59 is pushed through end sleeve 202 and shanks 234 and cups 232 pivot about rivet 254 in response to link arms 216 pivoting about pin 212 as the link arms are pushed out the end of sleeve 202. The ends of link arms 216 attached to shanks 234 pivot away from one another, thereby forcing the ends of the shanks 234 apart which causes cups 232 to separate thereby exposing trocar 242, best seen in FIG. 11. With trocar 242 lodged in the tissue sample, the operator retracts spool 44 so that the reverse of the jaw opening process occurs and cups 232 close together which acts to grip, cut and pull a tissue sample. The operator then retracts forceps device from endoscope 20 with the jaw assembly closed.

Jaw assembly 60 of the present invention is advantageous in that by using pins 240 integrally formed with jaw 230, two rivets less are needed. In addition, by virtue of interlocking tab 250 and grooved rivet 254, there are no sharp projections protruding from the side of the forceps device which could damage the endoscope and no components to become dislodged during cleaning and the like.

When the jaws are opened, ridge end face 102 bears against shoulder 114 thereby transmitting the forward movement of spool 44 to forward movement of cable 58. When the jaws are closed, end face 104 bears against surface 127 of split rim 126 thereby transmitting the backward movement of spool 44 into retracting movement of cable 58. In this way, no stress is experienced by bosses 128 during movement of the cable.

While the flexible biopsy forceps device disclosed herein has been described with respect to the illustrated embodiment, it will be appreciated that numerous variations of this embodiment may be made without departing from the scope of the invention as disclosed herein.

Therefore what is claimed is:

1. A biopsy forceps device, comprising;
   a) a flexible sheath and a cable extending through said flexible sheath;
   b) a jaw assembly operably coupled to one end of said cable and sheath; and
   c) a handle assembly operably coupled to said sheath, said handle assembly including a shaft member and a spool slidably mountable on said shaft, the spool having first locking means which are of unitary construction with the spool, including a spool insert receivable by the spool, the spool insert including second locking means which are of unitary construction with the spool insert, the first locking means lockingly engagable with the second locking means for irreversibly locking the spool insert and spool together, the other end of said cable operably coupled to said spool insert when the handle assembly is assembled, whereby movement of said spool on the shaft moves the cable with respect to the sheath for opening and closing the jaw assembly, wherein said spool includes as axial passageway extending therethrough, said spool insert comprising a pair of shell members which are generally half-cylindrically shaped and receivable within the axial passageway, wherein said first locking means comprises a pair of spaced slots located at a first end of the spool, including a pair of spaced ridges extending into said axial passageway and having ridge end portions spaced from a second end of the spool.

2. A biopsy forceps device according to claim 1 in which said second locking means comprises an outwardly protruding shoulder located at substantially a first end portion of each shell member and an outwardly protruding boss member located at a second end portion each shell member, the boss member being resiliently deformable and sized to fit into one of said slots, wherein the boss member and shoulder on each shell member are aligned along a line parallel to an elongate axis of the shell.

3. A biopsy forceps device according to claim 2 wherein one of said slots and one of said ridges are aligned along a first line parallel to said axial passageway, and the other slot and ridge are aligned along a second line parallel to the axial passageway, whereby the spool insert is received into the axial passageway with the shoulders located between the ridges until the shoulders pass the ends of the ridges and the spool is rotated until the boss members snap into the slots.

4. A biopsy forceps device according to claim 3 wherein said shaft member provided with a cylindrical portion and a bifurcated portion having two spaced rods, the pair of shell members slidably movable on said bifurcated portion.

5. A biopsy forceps device according to claim 3 wherein said cylindrical portion has an axial passageway extending therethrough which has a first portion having a first diameter suitable to receive an end portion of the sheath therein and a second portion having a smaller diameter suitable to receive the cable therethrough but not the sheath.

6. A biopsy forceps device according to claim 5 wherein the end of said cable coupled to said insert is secured in a cavity on the interior of said insert.

7. A biopsy forceps device according to claim 1 wherein said jaw assembly includes a bracket attached to said sheath, a pair of link arms pivotally attached to said one end of the cable, a pair of cups, each cup having a shank portion attached thereto, the shank portions pivotally attached to said pair of link arms, and a trocar disposed between said cups, the shank portions being pivotally connected to said bracket by a rivet extending through said bracket and holes in said shank portions.

8. A biopsy forceps device according to claim 7 wherein said trocar includes a mounting portion having a hole extending therethrough sized to receive said rivet, the trocar including a detent means projecting into said hole, said rivet including a slot for receiving said detent means for locking said trocar with respect to said rivet.

9. A biopsy forceps device, comprising;
   a) a flexible sheath and a cable extending through said flexible sheath;
   b) a jaw assembly operably coupled to one end of said cable and sheath; and
   c) a handle assembly operably coupled to said sheath, said handle assembly including a shaft member and a spool slidably mountable on said shaft, the spool having first locking means which are of unitary construction with said spool, said handle assembly including a spool insert receivable by said spool, the spool insert including second locking means which are of unitary construction with said spool insert, said spool including an axial passageway extending therethrough, said spool insert comprising a pair of shell members which are generally half-cylindrically shaped and receivable within said axial passageway, said first locking means comprising a pair of spaced slots located at a first end of the spool and a pair of spaced ridges extending into said axial passageway and having ridge end portions spaced from a second end of the spool, said second locking means comprising an outwardly protruding shoulder located at substantially a first end portion of each shell member and an outwardly protruding boss member located at a second end portion of each shell member, said boss member being resiliently deformable and sized to fit into one of said slots, wherein said boss member and shoulder on each shell member are aligned along a line parallel to an elongate axis of said shell, wherein one of said slots and one of said ridges are aligned along a first line parallel to said axial passageway, and said other slit and ridge are aligned along a second line parallel to said axial passageway, whereby said spool insert is received into said axial passageway with said shoulders located between said ridges until said shoulders pass said ridge end portions and said spool is rotated until said boss members snap into said slots, to irreversibly lock said spool insert and said spool together, another end of said cable operably coupled to said spool insert when said handle assembly is assembled, whereby movement of said spool on said shaft moves said cable with respect to said sheath for opening and closing said jaw assembly.

* * * * *

UNITED STATES PATENT AND TRADEMARK OFFICE
CERTIFICATE OF CORRECTION

PATENT NO. : 5,325,866
DATED : July 5, 1994
INVENTOR(S) : Jacek Krzyzanowski

It is certified that error appears in the above-indentified patent and that said Letters Patent is hereby corrected as shown below:

Column 7
Claim 1, line 57, please change "as" to --an--.

Claim 9, (column 8), line 56, please change "the" to --said--;
, line 60, please change "the" to --said--;
, line 68, please change "the" to --said--;
, (column 9), line 2, please change "the" to --said--; and
, line 14, please change "slit" to --slot--.

Signed and Sealed this

Twenty-ninth Day of November, 1994

Attest:

BRUCE LEHMAN

Attesting Officer     Commissioner of Patents and Trademarks